(12) United States Patent
Gazenko

(10) Patent No.: US 8,361,783 B2
(45) Date of Patent: *Jan. 29, 2013

(54) MICROMETHOD AND DEVICE FOR THE RAPID DETECTION, ENUMERATION AND IDENTIFICATION OF MICROORGANISMS

(75) Inventor: Sergey Gazenko, Mason, OH (US)

(73) Assignee: Nanologix, Inc., Hubbard, OH (US)

( * ) Notice: Subject to any disclaimer, the term of this patent is extended or adjusted under 35 U.S.C. 154(b) by 289 days.

This patent is subject to a terminal disclaimer.

(21) Appl. No.: 12/797,106

(22) Filed: Jun. 9, 2010

(65) Prior Publication Data

US 2010/0248350 A1 Sep. 30, 2010

Related U.S. Application Data

(63) Continuation-in-part of application No. 10/141,677, filed on May 9, 2002, now Pat. No. 7,781,159.

(51) Int. Cl.
*C12M 1/34* (2006.01)

(52) U.S. Cl. .......... 435/287.2; 427/2.3; 435/286.5; 436/518

(58) Field of Classification Search .......... None
See application file for complete search history.

(56) References Cited

U.S. PATENT DOCUMENTS

| | | | |
|---|---|---|---|
| 4,237,223 A | 12/1980 | Metz | |
| 4,317,726 A * | 3/1982 | Shepel | 210/236 |
| 5,624,815 A | 4/1997 | Grant et al. | |
| 5,650,323 A | 7/1997 | Root | |
| 5,660,990 A | 8/1997 | Rao et al. | |
| 5,716,798 A | 2/1998 | Monthony et al. | |
| 5,770,440 A | 6/1998 | Berndt | |
| 6,372,183 B1 | 4/2002 | Akong et al. | |
| 6,696,286 B1 | 2/2004 | Halverson et al. | |
| 6,729,352 B2 | 5/2004 | O'Connor et al. | |
| 6,743,581 B1 | 6/2004 | Vo-Dinh | |
| 6,767,706 B2 | 7/2004 | Quake et al. | |
| 6,818,435 B2 | 11/2004 | Carvalho et al. | |
| 6,852,222 B2 | 2/2005 | Lautenschlager et al. | |
| 2002/0187564 A1 * | 12/2002 | Chow et al. | 436/518 |
| 2002/0189374 A1 | 12/2002 | DeSilets et al. | |
| 2005/0009113 A1 | 1/2005 | Goldbard et al. | |
| 2006/0088895 A1 | 4/2006 | Wanders et al. | |

OTHER PUBLICATIONS

Oikonomakos et al., Influence of substrates and effectors on eosin-enzyme complexes, 1979, Biochem J, 181: pp. 309-320.*
Moorthy et al. "In situ fabricated porous filters for microsystems," Lab Chip, vol. 3 (Apr. 30, 2003), pp. 62-66.
Thiebaud et al "PDMS device for patterned application of microfluids to neuronal cells arranged by microcontact printing," Biosensors &Bioelectronics, vol. 17 (2002), pp. 87-93.
Walker et al. "Insect Cell Culture in Microfluidic Channels," Biomedical Microdevices, vol. 4, No. 3 (2002), pp. 161-166.

(Continued)

*Primary Examiner* — N. C. Yang
(74) *Attorney, Agent, or Firm* — Acker Wood IP Law, LLC; Gwen R. Acker Wood

(57) ABSTRACT

The present invention provides a device such as a medical device for the rapid detection, enumeration and identification of microorganisms. It is based on the production and accumulation of absorbent or fluorescent molecules during reactions between artificial substrates and enzymes in micro-channels of a sampling-detecting unit of the device. Enzymes of cells, or enzymes attached to cell bodies through antibody-enzyme conjugates, produce easily detectable concentrations of colored or fluorescent molecules in very small volumes, much faster than what is produced in conventional large volume devices. Microorganisms contained in the micro-channels appear as colored or fluorescent dots when viewed using a light or a fluorescent microscope.

14 Claims, 2 Drawing Sheets

OTHER PUBLICATIONS

Yang et al. "Cell docking and on-chip monitoring of cellular reactions with a controlled concentration gradient on a microfluidic device," Anal. Chem., vol. 74 (2002), pp. 3991-4001.

Martin et al. "Generation of larger numbers of separated microbial populations by cultivation in segmented-flow microdevices," Lab Chip, vol. 3 (May 23, 2003), pp. 202-207.

Mattman et al. "Cellophane Membranes in Growth of L. Variants of the Genus Proteus," Applied Microbiology, vol. 6, No. 2 (Mar. 1958), pp. 153-154.

Tse et al. "Membrane filter staining method: bacterial plate counts in 24 H," Applied and Environmental Microbiology, vol. 48, No. 2 (1984), pp. 433-434.

* cited by examiner

MICROMETHOD AND DEVICE FOR THE RAPID DETECTION, ENUMERATION AND IDENTIFICATION OF MICROORGANISMS

CROSS REFERENCE TO RELATED APPLICATIONS

This application is a continuation-in-part of U.S. application Ser. No. 10/141,677, filed May 9, 2002, which is incorporated herein by reference.

BACKGROUND OF THE INVENTION

Modern methods for the detection, enumeration and identification of microorganisms fall into two main categories. The first provides analysis after preliminary growth on a special nutrient media. The second category does not require preliminary growth. Methods utilized in the first category utilize several different chemical, biochemical, physical or optical techniques and require many hours or days for preliminary growth in order to produce enough homogeneous cells or colonies for detection. The second category utilizes methods of microscopy, flow cytometry or polymerase chain reaction (PCR). These methods allow for analysis immediately after sampling and sample treatment. Analyzing a single cell without preliminary growth belongs to these rapid micromethods.

Microscopy (light and fluorescent, visual or automated) and flow cytometry (absorbent, fluorescent or scattering) requires treatment of cells by absorbent or fluorescent dyes. Utilization of antibodies with attached fluorescent molecules helps in rapid identification of single cells. A higher concentration of colored molecules increases the reliability of analysis.

Well known markers for detection and identification of cells are artificial substrates, i.e., non-colored or fluorescent substances cleaved by enzymes or enzymatic groups with the production of light-absorbent or fluorescent molecules. Artificial substrates are broadly used for the detection of live microorganisms, detection by unique enzymes, identification by enzymatic profiles, or utilization in enzyme immunological analysis (EIA). Some artificial substrates produce non-soluble intracellular precipitates (e.g. tetrazolium salts, fluorescein-based substrates in acidic environments, Rezorufin and others). This feature is useful for microscopy and flow cytometry because of the production of specifically colored cell bodies. Other substrates produce soluble derivatives that are excreted from the cells and color the buffer solution (e.g. 4-Methylumbelliferone, tetramethylbenzidine, fluorescein in alkaline environments and others). This group of artificial substrates is able to produce a large amount of absorbent or fluorescent molecules because they do not accumulate in cells and do not interfere with biochemical pathways of living cells the way precipitates do.

Retention of fluorescent or absorbent molecules excreted from cells or produced in EIA in a small space around a single cell can easily create detectable concentrations of these molecules. Utilization of this useful feature of soluble absorbent or fluorescent molecules together with a simple hand-held device for cell sampling and then immediately treating cells for detection or identification purposes is the subject of the present invention.

Simple and rapid detection, enumeration and identification of single prokaryotic or eukaryotic cells is very important in medical microbiology, cytology, environmental science, detection of pollutant microorganisms in food, in the pharmaceutical industry, epidemiology, public and military defense, scientific research and other areas.

SUMMARY OF INVENTION

The present invention provides a device, such as a medical device, comprised of a sampling detecting unit (SDU) for the rapid detection, enumeration and/or identification of one or more microorganisms from liquid or air, based on the production and accumulation of absorbent or fluorescent molecules during reactions between artificial substrates (AS) and enzymes in micro-channels of the (SDU).

This invention differs from other rapid micromethods by utilizing a unique sampling detection unit, comprised of an array of long, parallel, similarly shaped and sized open-ended micro-channels for retaining the products of enzyme-substrate reactions from at least one single trapped cell. The processes of sampling and sample treatment occur in the same device. The device allows for the detection, identification and enumeration of single entities within the SDU with the use of fluorescent or light microscopes or other simple optical devices or automated instruments for microanalysis.

The SDU is comprised of a micro-channel plate having an upper surface and a lower surface. The micro-channel plate is comprised of a plurality of vertically elongated, parallel micro-channels which are open at the upper surface and lower surface of the micro-channel plate. The upper surface of a filter is located adjacent to the lower surface of the micro-channel plate, an intermediate layer is located adjacent to the lower surface of the filter and a solid base is located adjacent to the intermediate layer.

The medical device is further comprised of a cylindrical chamber having an upper end and a lower end surrounding the SDU. The cylindrical chamber is comprised of an inner cylinder and an outer cylinder, a moveable plunger located adjacent to the inner cylinder and a channel that can open or close within the cylindrical chamber adjacent to the SDU to allow equalization of air pressure inside and outside of the chamber. The opening and closing of the channel is achieved by rotating the inner cylinder against the outer cylinder. An orifice is located at the lower end of the cylindrical chamber. A removable cap can be placed over the orifice to close the opening.

In use, a liquid sample containing one or more microorganisms can be passed by pressing the sample down the cylindrical chamber by pressing down on the plunger. The sample passes down the cylindrical chamber in one direction from the upper end to the lower end of the chamber. The one or more microorganisms in the sample are trapped in the micro-channels on the upper surface of the filter.

An artificial substrate can be added to the micro-channels from the upper to the lower surface of the micro-channel plate to react with enzymes associated with, i.e., produced by, the one or more microorganisms contained within one or more of the plurality of micro-channels. After a period of incubation, this produces in one or more of the plurality of micro-channels one or more colored or fluorescent dots which allows for the detection, enumeration and identification of the one or more microorganisms.

In an exemplary embodiment, the detection, enumeration and identification is performed on a single microorganism without requiring preliminary growth of the single microorganism.

The addition of an artificial substrate to the micro-channels can be repeated a plurality of times on the micro-channel plate to obtain enzymatic profiles to identify a plurality of species of microorganisms from one sample.

The enzymes can be, for example, an antibody-enzyme conjugate that is attached to one of the one or more microorganisms. Fluorescent dots can be detected by fluorometry and colored dots can be detected by colorimetry.

The detection, enumeration and/or identification of the one or more microorganisms in the one or more micro-channels can be performed using an optical instrument such as a light microscope, a fluorescent microscope or other optical instruments.

BRIEF DESCRIPTION OF THE DRAWINGS

The drawings included herewith are incorporated in and form a part of this specification. The drawings illustrate one embodiment of the present disclosure and, together with the description, serve to explain the principles of the invention. It should be understood that drawings referred to in this description are not drawn to scale unless specifically noted.

DETAILED DESCRIPTION OF THE INVENTION

This invention provides a device, such as a medical device, comprised of a sampling detecting unit (SDU) having a plurality of micro-channels characterized by very small volumes for sampling at least one or more single cells from liquid or air; easy treatment procedures of the at least one or more cells trapped in the device; and retention of colored or fluorescent molecules which are products of reactions in the micro-channels to reach detectable concentrations of the at least one or more cells.

Figure 1:
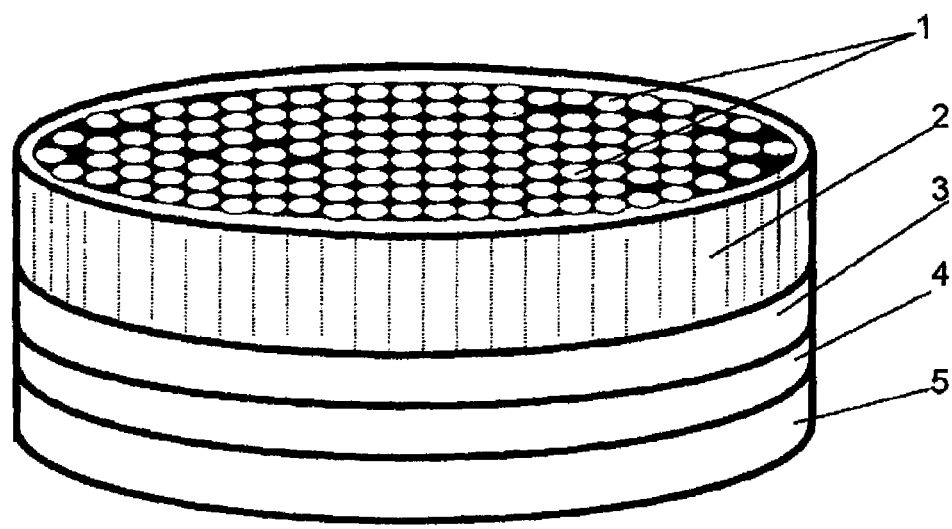
FIG. 1 is an isometric view of a sampling-detection unit (SDU) comprised of multiple micro-channels, a filter layer, an intermediate layer and a solid base.
Figure 2:
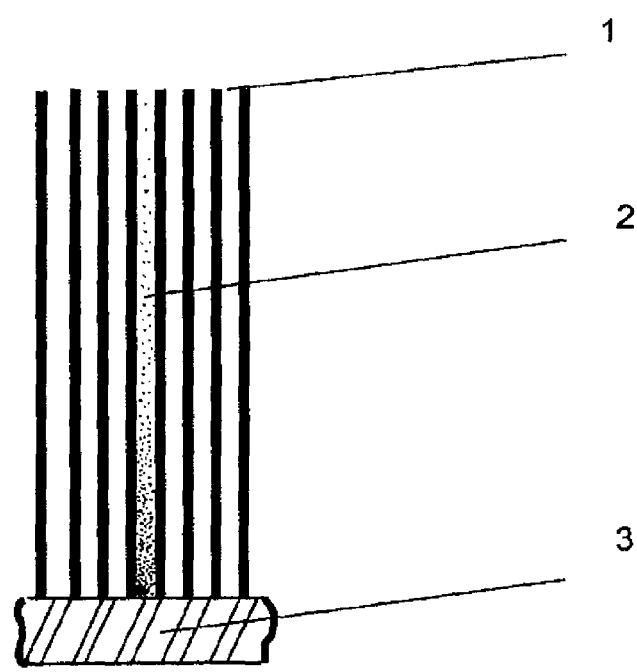
FIG. 2 is an enlarged cross-sectional view of several exemplary micro-channels, including one micro-channel showing trapped colored or fluorescent cells, and a filter layer.

Referring to FIGS. 1 and 2, the invention is based on the production and accumulation of absorbent or fluorescent molecules during reactions between artificial substrates (AS) and enzymes in micro-channels 1 of the SDU 2. The SDU 2 contains a plurality of micro-channels 1, a membrane filter, i.e., filter layer 3 for the retention of single particles or cells, an intermediate layer 4 and a solid base, i.e., rigid layer 5. Samples are filtered from liquid or air.

FIG. 2 shows enlarged micro-channels where one of the micro-channels contains a cell and colored molecules (1: upper orifice of the micro-channel; 2: a micro-channel with a cell and colored molecules; 3: a filter for trapping the cells). An optical object that is greater than a cell by a thousand to ten thousand times can easily be detected with light or fluorescent optics. The positive effect of the accumulation of the products of colored reactions in a very small volume is illustrated by the following calculations. One milliliter ($10^{12}$ µm$^3$) of liquid containing $25 \times 10^6$ cells is divided into smaller parts. Each 0.2 ml ($10^{12}$ µm$^3$; the well of 96-well plate) will contain $5 \times 10^6$ cells. One hundred cells will be in a volume of $4 \times 10^6$ µm$^3$. A volume of $4 \times 10^6$ µm$^3$ will contain only one cell. This volume corresponds to a micro-channel of an SDU with the following dimensions: diameter=10 µm; length=500 µm; volume approximately =39,000 µm$^3$. All of the volumes with cells, including the smallest, corresponds to a concentration of $25 \times 10^6$ cells/ml. This high concentration of cells can produce an easily detectable concentration of colored or fluorescent molecules from enzyme-artificial substrate reactions.

Figure 3:
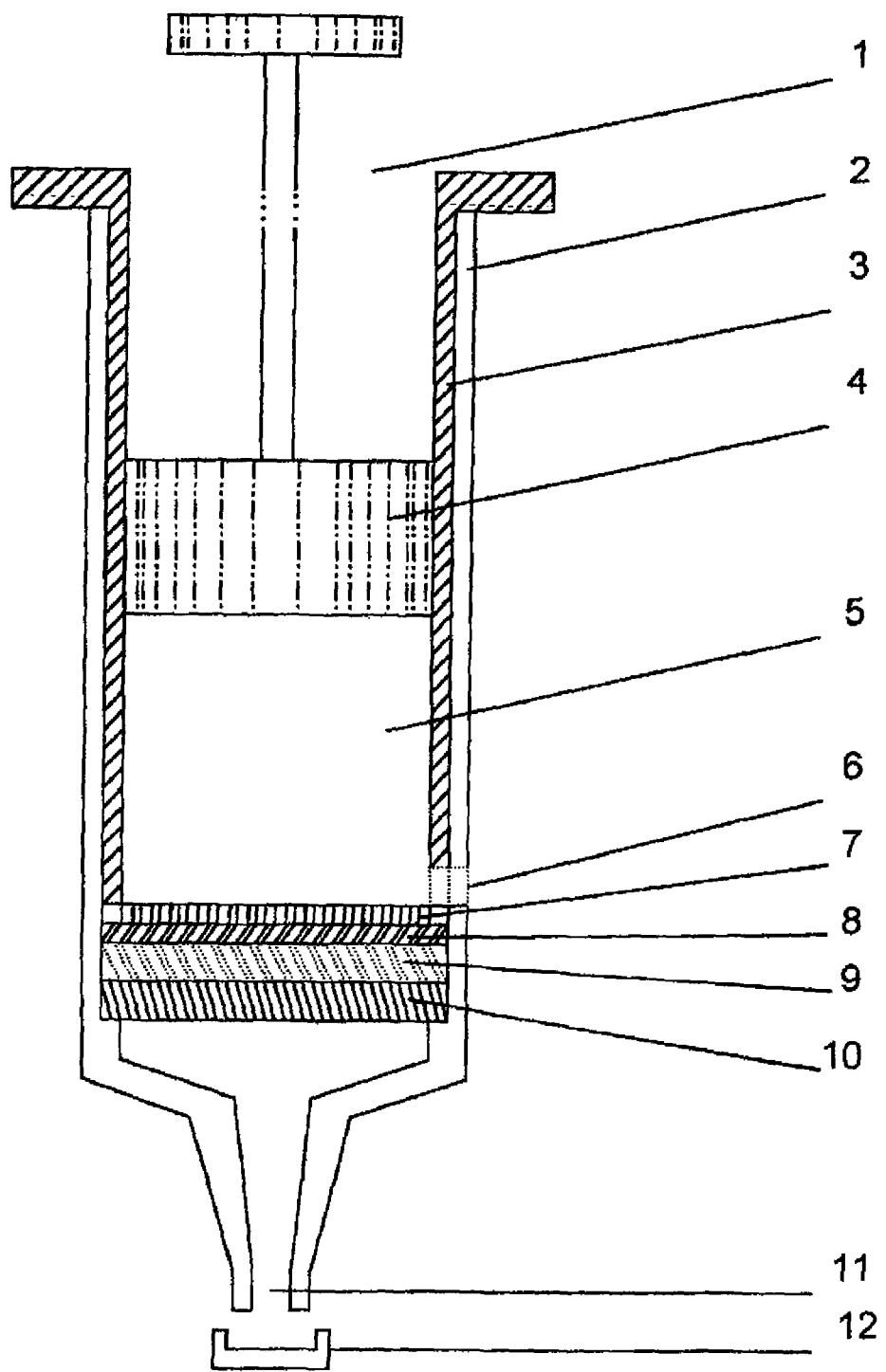
FIG. 3 is a cross-sectional view of a hand-held device for sampling and treatment of microorganisms.

As shown in FIG. 3, the SDU 7, 8, 9, 10 is part of a hand-held sampling device. It is well understood, and currently used in practice, that dividing a sample into small volumes helps to more quickly detect cell concentrations. This effect depends on reaching a detectable concentration in a small volume faster than in a large volume.

U.S. Pat. No. 5,716,798 discloses a method for rapid detection of microorganisms in a container divided into a plurality of discrete zones, each of which can be separately monitored for microbial presence by reaching detectable cell concentrations after preliminary growth in some zones. This method gives a timesaving of 10% to 40% in comparison with other methods. U.S. Pat. No. 5,770,440 discloses similar effects. The present invention differs from these disclosures by being able to analyze as little as one cell. No time consuming preliminary growth of cells or nutrient media are necessary.

U.S. Pat. No. 4,959,301 discloses dividing a sample with viable biological entities in several micro-droplets and detecting entities by growth or by biochemical reactions of a single entity within a droplet. This method can indicate a single cell in less than 30 minutes in some variants. Nevertheless, it is technologically complicated. Microdroplets are produced with different volumes and require statistical analysis for calculating results. This method can be reproduced in a laboratory only by using highly professional personnel.

In contrast, the present invention has the following advantages: the micro-channels each have an equal volume: no statistical analysis is necessary; droplets require special manipulation against drying, but because the micro-channels have a diameter/length=1/30-1/50, there is an extremely small degree of evaporation. Thus, no special action needs to be taken against drying of the droplets; the volume of a micro-channel is smaller than an average droplet, therefore detectable concentrations of an AS can be reached more quickly.

The increased detection of cell concentrations in small volumes also can be used in EIA and ELISA. Well-known 96-well immunological plates now are produced with 384 and 912 wells on a plate of the same size (128 mm×86 mm). A smaller volume provides the opportunity to reach a detectable concentration of absorbent or fluorescent molecules more quickly, or to use smaller concentrations of homogeneous cells. However, these plates and procedures of identification can only be used for identification of homogeneous cells in concentrations o hundreds to thousands of cells per ml.

The inventor's experiments and calculations have been done with vegetative cells such as *Bacillus cereus*. The experiments demonstrate that one live cell of *Bacillus cereus* (TSA, 17 hours at 3° C.) produces about 3,000,000 fluorescent molecules of 4-Methylumbelliferone (MU) from 4-Methilumbelliferyl acetate (MUA) per minute. To find fluorescence by the naked eye in the quartz cell of a fluorometer Perkin-Elmer L6 with a maximum excitation of 350 nm would require a concentration of MU of about $6 \times 10^{15}$ molecules per ml. This concentration in a volume of 0.01 mm$^3$ (10 µm$^3$) can be produced by one cell of *Bacillus cereus* in 2 minutes. To reach the same concentration in 0.1 mm$^3$ would require 33 hours of a one cell incubation; in 1 mm$^3$, 3.8 years of incubation would be required; 0.02 cm$^3$ would require 76 years; 0.2 cm$^3$ (the volume of a 96-well plate) would require 760 years; and a 1 cm$^3$ would require 3800 years of incubation!

Thus, the volumes for such reactions need to be as small as possible to reach a detectable concentration in an acceptable time frame, but large enough to be detected by simple optical methods. Modern rapid micro-methods based on the concentration of dye in a cell body (e.g., flow cytometry; automated microscopy) requires specialized complex techniques (e.g., scanning of a surface; special flow stream devices) to find a single cell on a filter, slide, or in a flow stream because of the very small size of an object, e.g., about 0.5 to 5.0 µm³.

The size of the object (fluorescent or colored micro-channel) according to the present invention is thousands to tens of thousands times larger. Therefore, simple optics with small multiplication can be employed with no specialized, complex techniques required to visualize the results. Thus, the present invention can be employed in field studies and does not require high level professionals. The price of analysis can also be significantly reduced.

Another important aspect of this invention is the usage of artificial substrates for different enzymes or enzymatic groups for the production of detectable concentrations of absorbent or fluorescent molecules. Artificial substrates are broadly used for detection of enzymatic activities. Many different artificial substrates are based on chromogenic molecules such as 2-Nitrophenol, 4-Nitrophenol, 5-4-chloro-3-indoxol, 3-Indoxol, 5-Bromo-6-chloro-3-indoxol, 6-Chloro-3-indoxol, 5-Iodo-3-indoxol, N-Methylindoxol, 3,3',5,5'-Tetramethylbenzidine dihydrochloride and others. Other artificial substrates are based on fluorescent molecules such as 4-Methylumbelliforone, 7-Amido-4-methylcoumarin, Fluorescein and Eosine. They cover a large spectrum of different enzymes such as Glycosidases, Esterases, Phosphatases, Peptidases, Sulfatases, Dehydrogenases and special enzymes like Horseradish-Peroxidase, β-D-galactosidase or specific aminopeptidases.

Different analytical methods can be produced using the device of the present invention. Detection of a single live microorganism in a sample can be done with the use of artificial substrates for large groups of enzymes that are always present in live microorganisms. For example, 4-Methylumbelliferyl phosphate for phosphatases, 4-Methylumbellyferyl acetate for esterases, or a mixture or both can be used. Detection of several important microorganisms can also be done following identification of their unique enzymes. For example, 4-Methylumbelliferyl-B-D-galactopyranoside is a reliable indicator of β-D-galactosidase, a unique enzyme of *Escherichia coli*.

Identification of a single cell trapped in a micro-channel can be done with an enzyme attached to an antibody, which attaches to antigens of an investigated cell, e.g., an EIA version for a single cell.

Identification of a single cell can also be performed by enzymatic profiles. In this aspect, a trapped cell will produce a fluorescent product from a first substrate, which will be measured by the amount of its fluorescence and then washed out. After that, a second substrate will be applied and measured, followed by a third and so on. No special instrument currently exists for this purpose.

Procedure for Sampling and Treatment

Reaction Enzyme(s) and artificial substrate(s) are placed in the micro-channels of the SDU 1 (FIG. 1; the size of the openings of the micro-channels is much smaller than shown). The SDU is a part of the device for sampling and trapping of one or more cells (if present in a sample) in the micro-channels. Treatment procedures carried out in the device include accurate addition of artificial substrate solution(s), antibody-enzyme complex(es) and other reagents, if needed, to each micro-channel and washing solutions for rinsing (for example, surplus of antibody-enzyme complex(es) or during changing artificial substrates when profiles are investigated). All liquids pass through the device from the upper to the lower end to prevent releasing trapped cells from the micro-channels.

The general principle of the hand-held device of the present invention, as shown in FIG. 3, works as follows:

1. A liquid sample, possibly containing microorganisms, is placed in the chamber 5 of the device.

2. A plunger 4 presses the sample through the SDU 7-10. Cells, is present, are trapped in the micro-channels 7 on the surface of the filter 8.

3. A cap 12 closes the orifice, or opening 11. Rotation of the inner cylinder 3 against the outer cylinder 2 opens a channel 6 to equalize air pressure and to prevent reverse exit of trapped cells from the micro-channels 7. The channel 6 for pressure equalization can have any suitable type of construction, e.g., closing and opening of the channel 6 can done by using a spigot.

4. A small amount(s) of artificial substrate(s) is added to the chamber 5 of the device and the plunger 4 presses it into all of the micro-channels 7 of the SDU 7-10.

5. The device is incubated for several minutes to about 1 hour at room temperature or higher. Incubation time depends on the entity of interest being analyzed.

6. The device is untwisted and the SDU 7-10 is placed under a light or fluorescent microscope, scanning microscope or other optical instrument.

7. As shown in FIG. 2, the micro-channels 2 containing live cells appear as colored (absorbent version) or fluorescent dots. The diameter of the dots are about 15 µm (length of each micro-channel=500 µm and volume=88,000 µm³), for example, but could be bigger or smaller. This size is big enough to use a small magnification microscope: 40× to 100×. The use of small magnification allows for a rapid scan of the entire SDU surface, for example, several minutes, in order to detect and enumerate even one live cell. Automation of this process with micro-scanning systems can make this process faster.

Referring again to FIG. 3, in the case of identification by EIA for a single cell, the following protocol steps are added after step 3:

3'. A solution of conjugated antibody with a marker enzyme is added to the chamber 5. The mixture is incubated for the time required to attach the conjugate to antigens of interest.

3". The channel 6 is opened for equalization of pressure. The plunger 4 is pulled up and the device chamber is rinsed with a washing fluid that is pressed through with the plunger 4. This procedure can be done more than one time if needed.

In case of enzymatic profiles, steps 4, 5, 6 and 7 can be repeated a number of times. The level of absorption or fluorescence in the micro-channels can be measured by a micro-photometrical or micro-fluorimetrical instrument. This method allows for the identification of many different species in one sample, but it is more time consuming and complicated than the EIA method for identification of type of cell.

In the case of bioaerosol sampling, steps 1, 2 and 3 are adjusted as follows. Bioaerosol sampling can be performed after removal of the plunger 4 from the device and negative air pressure is maintained by placing the cap 11 into the orifice 12.

Identification of single virus particles also are possible by the present invention (e.g., EIA version for single virus particles). Trapping of single virus particles in the SDU can be performed the use of special filters such as membranes (e.g., dialysis membranes), treating the inner walls of the micro-channels with specific antibodies, lectines or other reagents, or use of magnetic particles.

EXAMPLES

The present invention is more particularly described in the following non-limiting examples, which are intended to be illustrative only, as numerous modifications and variations therein will be apparent to those skilled in the art.

Example 1

Detection of Live *Escherichia coli* Cells from Drinking Water

A 100 ml sample of water was pressed through the device and SDU of the invention having a black non-fluorescent nitrocellulose filter. Two ml of freshly made 4-Methylumbelliferyl-Beta-Dglucuronide (0.1 mg/ml) fluorogenic substrate in distilled water was pressed through the SDU. All microchannels were filled with the solution of fluorogenic substrate. The device was incubated for 20 minutes at 40 degrees C. After incubation, the device was untwisted and the microchannel plate and filter were placed under a fluorescent microscope: 60×; λ excitation: 340-380 nm; λ fluorescence: 450 nm. Micro-channels containing live *E. coli* appeared as blue fluorescent dots. Micro-channels without cells or live cells of other species appeared as black dots. The same results performed by other rapid methods could only be reached after 6-8 hours.

Example 2

Identification of *Brucella melitensis* from Milk

A 100 ml sample of milk previously defatted was pressed through a the device and SDU of the invention having a white nitrocellulose filter. Fifty ml of phosphate buffer, pH 8.0, was pressed through the device to wash out proteins and fat. Two ml of standard conjugated antibody for *B. melitensis* surface antigens and Horseradish Peroxidase were added to the device and slowly—part after part, during several minutes—pressed through the SDU. Fifty ml of distilled water then was pressed through the SDU to wash out the rest of the conjugate. Two ml of a solution of 3,3',5,5'-Tetramethylbenzidine was added to the device and pressed through the SDU. The device was incubated for 40 minutes at 35 degrees C. After incubation, the SDU and filter were placed under a light microscope: 60×. Micro-channels containing *B. melitensis* appeared as blue dots. Other micro-channels appeared as white dots. Even one cell in 100 ml could be found in less than one hour. Prior art procedures require a preliminary growth period of at least 26-28 hours. Flow cytometry require approximately the same amount of time as the method described herein, but requires the use of an instrument having a price of around $100,000 and highly qualified personnel. PCR provides the same results as reported herein in about two hours but involves a much more complicated technique.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A medical device for the rapid detection, enumeration and/or identification of one or more microorganisms, comprising:

a sampling detecting unit (SDU) comprised of a micro-channel plate having an upper surface and a lower surface, said micro-channel plate having formed therein a plurality of vertically elongated, parallel micro-channels which are open at said upper surface and at said lower surface of said micro-channel plate;

a filter having an upper surface and a lower surface, said upper surface of said filter positioned adjacent to said lower surface of said micro-channel plate;

an intermediate layer adjacent said lower surface of said filter; and a base adjacent said intermediate layer;

a cylindrical chamber having an upper end and a lower end surrounding said SDU, said cylindrical chamber comprised of an inner cylinder and an outer cylinder;

a moveable plunger located adjacent said inner cylinder;

a channel that can open or close within said cylindrical chamber adjacent to said SDU to allow equalization of air pressure inside and outside of said chamber, said opening or closing of said channel performed by rotating said inner cylinder against said outer cylinder;

an orifice located at said lower end of said cylindrical chamber; and a removable cap located at lower end of said cylindrical chamber.

2. The medical device of claim 1, wherein a liquid sample containing one or more microorganisms can be passed in said cylindrical chamber in one direction from said upper end of said chamber to said lower end of said chamber and are trapped in said plurality of micro-channels on the surface of said filter.

3. The medical device of claim 2, wherein passing said liquid sample is performed by pressing the sample down said cylindrical chamber by pressing down on said moveable plunger.

4. The medical device of claim 3, wherein an artificial substrate may be passed in said cylindrical chamber in one direction from said upper end of said chamber to said lower end of said chamber and are trapped in said plurality of micro-channels on the surface of said filter in order to react with an enzyme associated with said one or more microorganisms contained within one or more of said plurality of micro-channels after a period of incubation to produce in one or more of said plurality of micro-channels one or more colored or fluorescent dots in order to detect, enumerate and identify said one or more microorganisms.

5. The medical device of claim 4, wherein said enzyme associated with said one or more microorganisms is produced by one of said one or more microorganisms.

6. The medical device of claim 5, wherein said enzyme associated with said one or more microorganisms is an antibody-enzyme conjugate that is attached to one of said one or more microorganisms.

7. The medical device of claim 4, wherein said artificial substrate is selected from the group consisting of 2-Nitrophenol, 4-Nitrophenol, 5-4-chloro-3-indoxol, 3-Indoxol, 5-Bromo-6-chloro-3-indoxol, 6-Chloro-3-indoxol, 5-Iodo-3-indoxol, N-Methylindoxol, 3,3',5,5'-Tetramethylbenzidine dihydrochloride, 4-Methylumbelliforone, 7-Amido-4-methylcoumarin, Fluorescein and Eosine.

8. The medical device of claim 4, wherein said one or more fluorescent dots are detected by fluorometry.

9. The medical device of claim 4, wherein said one or more colored dots are detected by colorimetry.

10. The medical device of claim 1, wherein the detection, enumeration and/or identification of said one or more microorganisms in said plurality of micro-channels is performed with an optical instrument.

11. The medical device of claim 10, wherein the optical instrument is selected from the group consisting of a light microscope, a fluorescent microscope and other optical instruments.

12. The medical device of claim 4, wherein passing the artificial substrate in said cylindrical chamber in one direction from said upper end of said chamber to said lower end of said chamber and being trapped in said plurality of micro-channels on the surface of said filter in order to react with an enzyme associated with said one or more microorganisms contained within one or more of said plurality of micro-channels after a period of incubation to produce in one or more of said plurality of micro-channels one or more colored or fluorescent dots in order to detect, enumerate and identify said one or more microorganisms can be repeated a plurality of times in said cylindrical chamber to obtain enzymatic profiles to identify a plurality of species of microorganisms from one sample.

13. The medical device of claim 12, wherein said device allows for the detection, enumeration and/or identification of a single microorganism without requiring preliminary growth of said single microorganism.

14. A device for the rapid detection, enumeration and/or identification of one or more microorganisms, comprising:
  a sampling detecting unit (SDU) comprised of a micro-channel plate having an upper surface and a lower surface, said micro-channel plate having formed therein a plurality of vertically elongated, parallel micro-channels which are open at said upper surface and at said lower surface of said micro-channel plate;
  a filter having an upper surface and a lower surface, said upper surface of said filter positioned adjacent to said lower surface of said micro-channel plate;
  an intermediate layer adjacent said lower surface of said filter; and a base adjacent said intermediate layer;
  a cylindrical chamber having an upper end and a lower end surrounding said SDU, said cylindrical chamber comprised of an inner cylinder and an outer cylinder;
  a moveable plunger located adjacent said inner cylinder;
  a channel that can open or close within said cylindrical chamber adjacent to said SDU to allow equalization of air pressure inside and outside of said chamber, said opening or closing of said channel performed by rotating said inner cylinder against said outer cylinder;
  an orifice located at said lower end of said cylindrical chamber; and
  a removable cap located at lower end of said cylindrical chamber.

* * * * *